US012558311B1

(12) United States Patent
Kershman et al.

(10) Patent No.: US 12,558,311 B1
(45) Date of Patent: *Feb. 24, 2026

(54) TRANS-MUCOSAL DELIVERY SYSTEM FOR TESTOSTERONE

(71) Applicant: Shear Kershman Laboratories, Inc., Chesterfield, MO (US)

(72) Inventors: Alvin Kershman, Chesterfield, MO (US); Jeff L Shear, Bonita Springs, FL (US)

( * ) Notice: Subject to any disclaimer, the term of this patent is extended or adjusted under 35 U.S.C. 154(b) by 141 days.

This patent is subject to a terminal disclaimer.

(21) Appl. No.: 18/355,924

(22) Filed: Jul. 20, 2023

Related U.S. Application Data

(63) Continuation of application No. 16/740,007, filed on Jan. 10, 2020, now Pat. No. 11,813,354.

(60) Provisional application No. 62/791,346, filed on Jan. 11, 2019.

(51) Int. Cl.
| | |
|---|---|
| *A61K 9/00* | (2006.01) |
| *A61K 9/107* | (2006.01) |
| *A61K 31/568* | (2006.01) |
| *A61K 47/10* | (2017.01) |
| *A61K 47/12* | (2006.01) |
| *A61K 47/14* | (2017.01) |
| *A61K 47/26* | (2006.01) |
| *A61K 47/44* | (2017.01) |

(52) U.S. Cl.
CPC ............ *A61K 9/0053* (2013.01); *A61K 9/107* (2013.01); *A61K 31/568* (2013.01); *A61K 47/10* (2013.01); *A61K 47/12* (2013.01); *A61K 47/14* (2013.01); *A61K 47/26* (2013.01); *A61K 47/44* (2013.01)

(58) Field of Classification Search
CPC .... A61K 9/0053; A61K 9/107; A61K 31/568; A61K 47/10; A61K 47/12; A61K 47/14; A61K 47/26; A61K 47/44
See application file for complete search history.

(56) References Cited

U.S. PATENT DOCUMENTS

2006/0078580 A1 * 4/2006 Dechow .................. A61P 31/10
424/61

FOREIGN PATENT DOCUMENTS

WO WO-0141732 A1 * 6/2001 ........... A61K 9/0043

OTHER PUBLICATIONS

Murashova (Effects of Oleic Acid and Phospholipids on the Formation of Lecithin Organogel and Microemulsion) (Year: 2018).*

* cited by examiner

*Primary Examiner* — Robert A Wax
*Assistant Examiner* — Quanglong N Truong
(74) *Attorney, Agent, or Firm* — Dentons US LLP; Derek A Auito

(57) ABSTRACT

A trans-mucosal testosterone delivery composition for humans or animals having from about 50 to 99 wt. % humectant, from about 1 to 50 wt. % water, from about 0.001 to 25.00 wt. % testosterone, from about 0 to 25 wt. % oil, and from about 25 to 1 wt. % surfactant, wherein the composition is hydrophobic and has release properties.

15 Claims, 5 Drawing Sheets

TRANS-MUCOSAL DELIVERY SYSTEM FOR TESTOSTERONE

CROSS-REFERENCE TO RELATED APPLICATIONS

This application claims the benefit of provisional patent application 62/791,346, filed Jan. 11, 2019, and utility patent application Ser. No. 16/740,007 filed Jan. 10, 2020, which are hereby incorporated by reference.

STATEMENT REGARDING FEDERALLY SPONSORED RESEARCH

Not Applicable

APPENDIX

Not Applicable.

BACKGROUND OF THE INVENTION

Field of the Invention

The present invention relates to a trans-mucosal delivery system for testosterone, and more particularly to a buccal delivery system for free testosterone.

Related Art

Drug efficacy generally depends upon the ability of the drug to reach its target in sufficient quantity to maintain therapeutic levels for the desired time period. Orally administered drugs must overcome several obstacles to reach their desired targets. Before orally administered drugs enter the general circulation of the human body, they are absorbed into the capillaries and veins of the upper gastrointestinal tract and are transported by the portal vein to the liver. The pH and enzymatic activities found in gastrointestinal fluids may inactivate the drug or cause the drug to dissolve poorly and not be absorbed. In addition, following their absorption in the intestine, orally administered drugs are often subject to a "first pass" clearance by the liver and excreted into bile or converted into pharmacologically inactive metabolites.

The oral administration of hormones, such as testosterone or estrogen, have proven challenging. Testosterone is administered orally in a bonded form as testosterone undecanoate, methyltestosterone, or testosterone cyclodextrin, to avoid the first pass effect. The bonded form is typically administered with food consumption. When administered in a regiment of hormone replacement therapy, it is desired to have sustained release properties, yet these forms of testosterone must be taken multiple times daily.

Of particular interest is the delivery of the native form of testosterone. The native form of testosterone is more stable than its bonded predecessors. More of the active ingredient is delivered in a smaller dosage and tablet form. It is a simpler and less expensive manufacturing process that eliminates the additional step of bonding the testosterone.

Testosterone may be administered by intramuscular injection as an oily solution or an aqueous suspension but, when administered by this route, testosterone is rapidly absorbed, metabolized and excreted. Testosterone esters are more hydrophobic than the free steroid and, consequently, are absorbed more slowly than testosterone from the intramuscular route. However, no rate-controlling mechanism is provided and intramuscular injection of a testosterone ester cannot, therefore, provide a substantially zero order pattern of release.

Transdermal administration avoids first-pass hepatic metabolism. However, the physical size of transdermal drug delivery systems is such that a new device must be used every few days. This can lead co fluctuations in circulating serum testosterone levels. Furthermore, frequent device replacement is inconvenient and has possible compliance problems for the patient. Although transdermal delivery systems that can maintain substantially constant delivery are known, it is not possible to maintain a substantially zero order delivery for at least three weeks by this route.

Subcutaneous implantation (50 or 100 mg) of testosterone-loaded pellets provides therapy extending to several months and is therefore advantageous in respect of both patient compliance and convenience. However, subcutaneous implants have a number of disadvantages. Specifically, a surgical procedure is required for both insertion and removal of the pellets. In addition, infection, pain and swelling can arise at the insertion site. Furthermore, due to physical size limitations of such systems, it is not possible to make testosterone implants that can deliver the hormone in a substantially zero order pattern over a prolonged period of at least three weeks.

None of the above devices or method disclose the present invention providing trans-mucosal delivery of testosterone.

SUMMARY OF THE INVENTION

The present invention relates to a trans-mucosal delivery form of testosterone for humans and animals made by combining an aqueous phase containing water and at least one humectant, wherein the at least one humectant is present in the aqueous phase in the range of from 1 to 99 wt. %.; and an oil phase comprising testosterone in the range of about 0.001 to 25.0 wt. %, optionally at least one surfactant, and optionally at least one oil; wherein the surfactant is present in the oil in the range of from about 1 to 99.999 wt. %. The aqueous phase is added to the oil phase in a weight ratio of about 3:1 to 49:1, and wherein the aqueous phase is added to the oil phase using low to medium shear mixing to provide the delivery system, and wherein the delivery system is hydrophobic and has release properties.

In a preferred embodiment, the oil phase comprises at least one oil and at least one surfactant, wherein the surfactant has a HLB of less than 4.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

THE DRAWINGS

The present invention will become more fully understood from the detailed description and the accompanying drawings, wherein.

3

Figure 3:
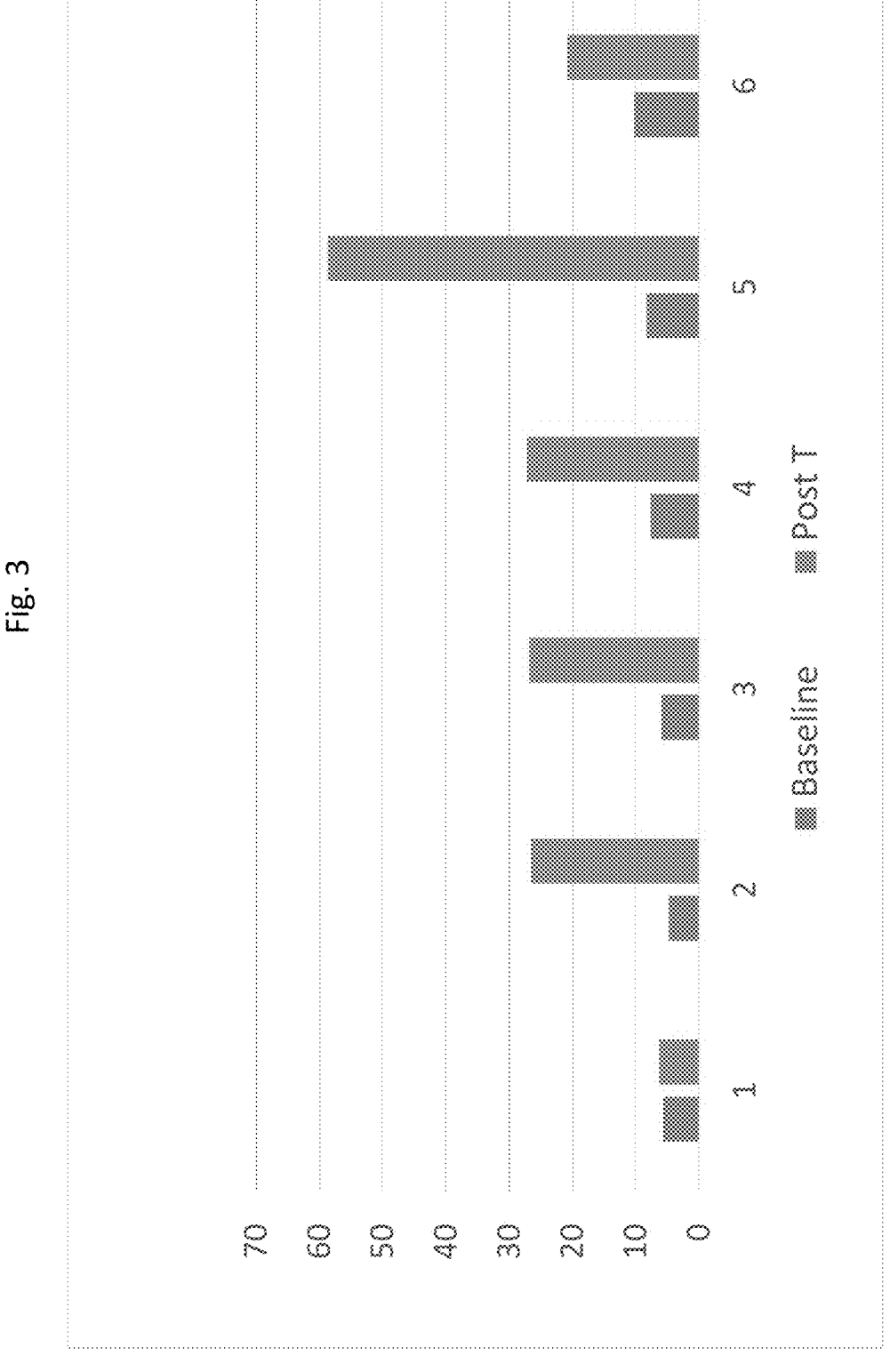

FIG. 3 is a bar graph of 6 male subjects showing an increase in blood serum levels after being buccally administered the present invention.

Figure 4:
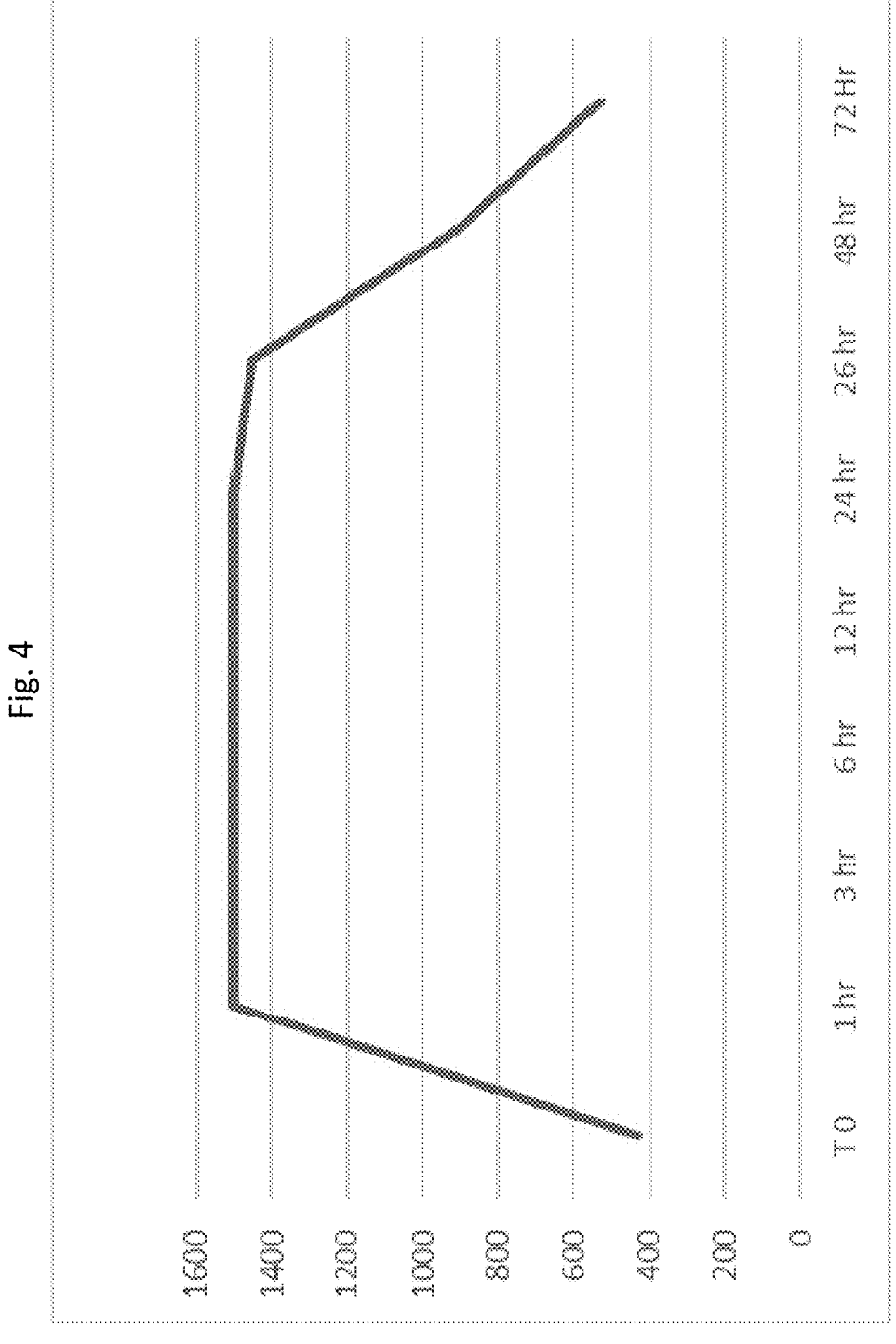

FIG. 4 show the results of a pharmacokinetic study of the present invention administered to the outer lip of male subjects.

Figure 5:
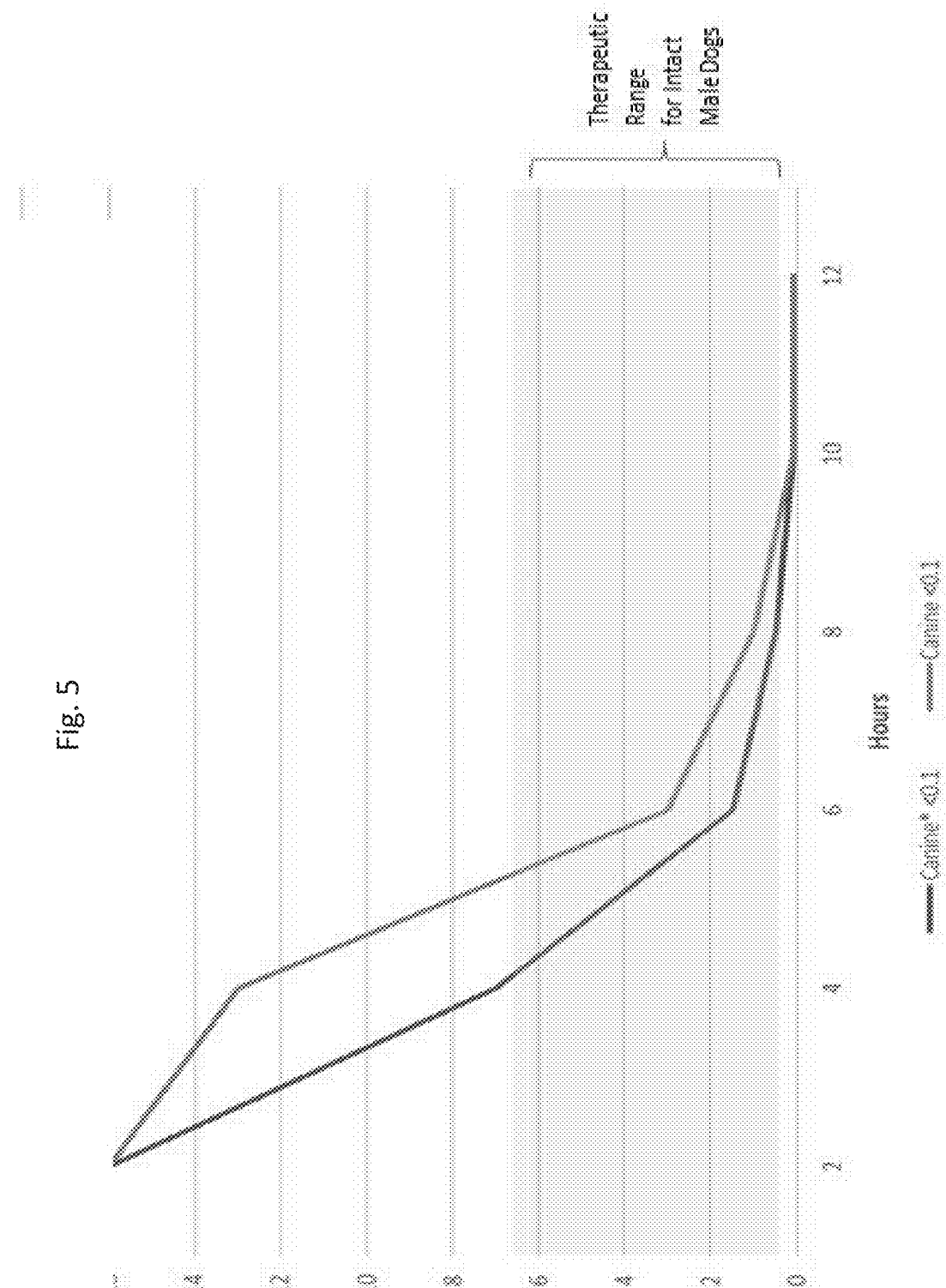

FIG. 5 show the results of a pharmacokinetic study of the present invention administered to the gums of male neutered dogs.

DETAILED DESCRIPTION OF THE PREFERRED EMBODIMENTS

The following description of the preferred embodiment(s) is merely exemplary in nature and is in no way intended to limit the invention, its application, or uses.

The oil phase is prepared from a hydrophobic solution or mixture containing optionally at least one oil or petroleum distillate and at least one surfactant. The surfactant is preferably a non-water soluble surfactant having an HLB number of less than 4, and includes emulsifiers. Examples of suitable surfactants include oleic acid, acetylated monoglycerides, glycerol dioleate, sorbitan tristearate, glycerol monoleate, acetylated monoglycerides and various combinations of these. A preferred surfactant is commercially sold as ATMOS 300K, and is a combination of mono- and di-glycerides made from edible food sources and propylene glycol.

The testosterone, which is oil soluble, is present in the oil phase. Preferably, the testosterone is added to the oil phase as granulated testosterone.

The surfactant is present in the oil phase in the amount of about 1 to 99.999%. The optional oil suitable for the oil phase is typically liquid or semi-solid at room temperature, and is compatible with the oral cavity. Such oils include plant oils, such as vegetable oil, corn oil, canola oil, coconut oil, castor oil or olive oil, and animal fats such as tallow and lard. The oils include petroleum distillates, such as petrolatum and mineral oil. Mixtures of oils are also contemplated in the present invention. The oil phase is present in the composition in the range of from about 2 to 25 wt. %. Preferably, the surfactant is present in the composition in the range of about 5 to 15 wt. %. In a preferred embodiment, the oil and the surfactant are present in the composition in a weight ratio of about 2:1 to 1:2.

The aqueous phase contains at least one humectant. Suitable humectants include, but are not limited to glycerin, lactic acid, polyols, propylene glycol, corn syrup, high fructose corn syrup (HFCS), including Cornsweet 55 and Cornsweet 42, and sorbitol. A preferred combination of humectants is glycerin and Cornsweet 55, which contains about 55 wt. % fructose, 21 wt. % glucose and 24 wt. % water. A preferred form of sorbitol is non-crystallizing liquid sorbitol (70 wt. % sorbitol in water). The ratio of glycerin to HFCS is from 1:1 to 10:1. Preferably, the ratio is about 4:1 to 10:1, and most preferably, about 7:1. The ratio of glycerin to non-crystallizing liquid sorbitol is in the range of about 2:1 to 1:2. The at least one humectant is present in the aqueous phase from 1 to 99 wt. %. The amount of at least one humectant in the composition is from about 1 to 99 wt. %. Preferably, the amount of humectant in the composition is from about 50 to 99 wt. %. More preferably, the amount of humectant in the composition is from about 75 to 99 wt. %.

Other additives suitable for the present invention include, but are not limited to colorings, flavorings and abrasives.

The claimed composition is typically prepared using a planetary or counter rotating type mixer having a rubber lined mixing bowl equipped with a rubber coated wire whip stirring device. The aqueous phase is blended at relatively low shear (30-600 rpm's) into the oil phase, continuously forming a total encapsulation of the aqueous solution droplets by the oil. This process is enhanced significantly by the oil wet-able properties of the rubber lining of the mixing bowl. Rubber coating of the wire whip device improves the rate of processing.

In an embodiment of the invention, the process of preparing the composition is conducted in 2 steps:

Step 1 produces a seed batch for further processing. The initial seed batch is produced by adding a small volume of oil phase to the lined mixing chamber or bowl at a sufficient depth that the wire whip or mixing device touches the oil while rotating. The wire whip is then engaged at rate of about 30 to 100 rpm's. The aqueous phase is added at a rate approximately equivalent to the initial volume of the oil solution per minute. That is, if the initial volume of the oil phase is 20 mL, then the aqueous phase is added at a rate of about 20 mL per minute while being mixed in at 30 to 100 rpm's. Once, the desired weight ratio of aqueous phase to oil phase is reached (about 3:1 to 49:1), this initial process step is concluded.

Step 2 begins with the seed batch of Step 1, at the desired final weight ratio of aqueous phase to oil phase. The volume of seed material needed for Step 2 is to about 5-20 volume % of the final mixing chamber volume. The mixing whip or equivalent stirring and folding device are engaged at a speed of about 50 to 600 rpm's. The oil and water phases are added separately and simultaneously to the starter batch at a ratio equal to that contained in the seed batch. The rate of adding the two separate solutions is about 1 to 5% of the mixing chamber capacity per minute. As the mixing bowl or chamber fills, excess liquid may be removed continuously without halting the process. Alternatively, the process can be halted for partial or entire contents removal. Once the process is halted and a portion of the contents removed, the retained material can be held for an extended period of time. Because coating of and encapsulation of the aqueous phase is almost immediate, and materials are mixed at final required ratio in step 2, all product produced at any time during step 2 is ready to use.

Another embodiment is shown in Example 1, below

Example 1

TABLE 1

| 20% TESTOSTERONE Batch Formula Calculator | | | |
| --- | --- | --- | --- |
| RM # | Ingredient | Weight g | % |
| 720 | Atmos 300K-surfactant | 97.5 | 7.50% |
| 1502 | Sweet Almond Oil | 32.5 | 2.50% |
| 1261 | Peppermint Terpeneless Oil | 6.5 | 0.50% |
| 223 | Testosterone Micro USP | 260.0 | 20.00% |
| 995 | Glycerin, USP 99.7% humectant | 773.5 | 59.50% |
| 1176 | Cornsweet 55 humectant (55 wt. % fructose, 21 wt. % glucose, 24 wt. % water) | 130 | 10.00% (2.4% water, 7.6% sugar) |
| T0tal | | 1300.00 | |

Method of Preparing the Testosterone System

A. Preparing Oil Phase Containing Testosterone (30.5 wt. % of Final Composition)

1. Warm Sweet almond oil and peppermint terpeneless to 26.7° C.

2. Add Atmos® 300K and testosterone, mix well and set aside.

B. Preparing the Aqueous Phase (69.5 wt. % of the Final Composition)

1. Mix the Cornsweet 55 solution and glycerin together. Mix well and warm to 43.33° C.

2. Remove heat source.

C. Forming the Lotion

1. Using a 5 quart lab Hobart type planetary lab/kitchen mixer with a rubber or plastic lined wire whip and rubber or plastic lined bowl add 40 g of oil phase and stir on #2 setting.

2. Slowly add approx. 200-300 g aqueous phase with mixing.

3. Add remainder of the oil phase to the bowl. Slowly add remainder of the aqueous phase to the bowl with mixing. Scrape the sides of the bowl with a spatula to ensure thorough mixing.

4. Increase the speed to #4 for 10 minutes more, making sure to scrape the sides of the bowl occasionally. After 10 minutes, the lotion is prepared.

The lotion of Example 1, Table 1, above, is viscous, pourable, non-water dispersible and has release properties.

Figure 1:
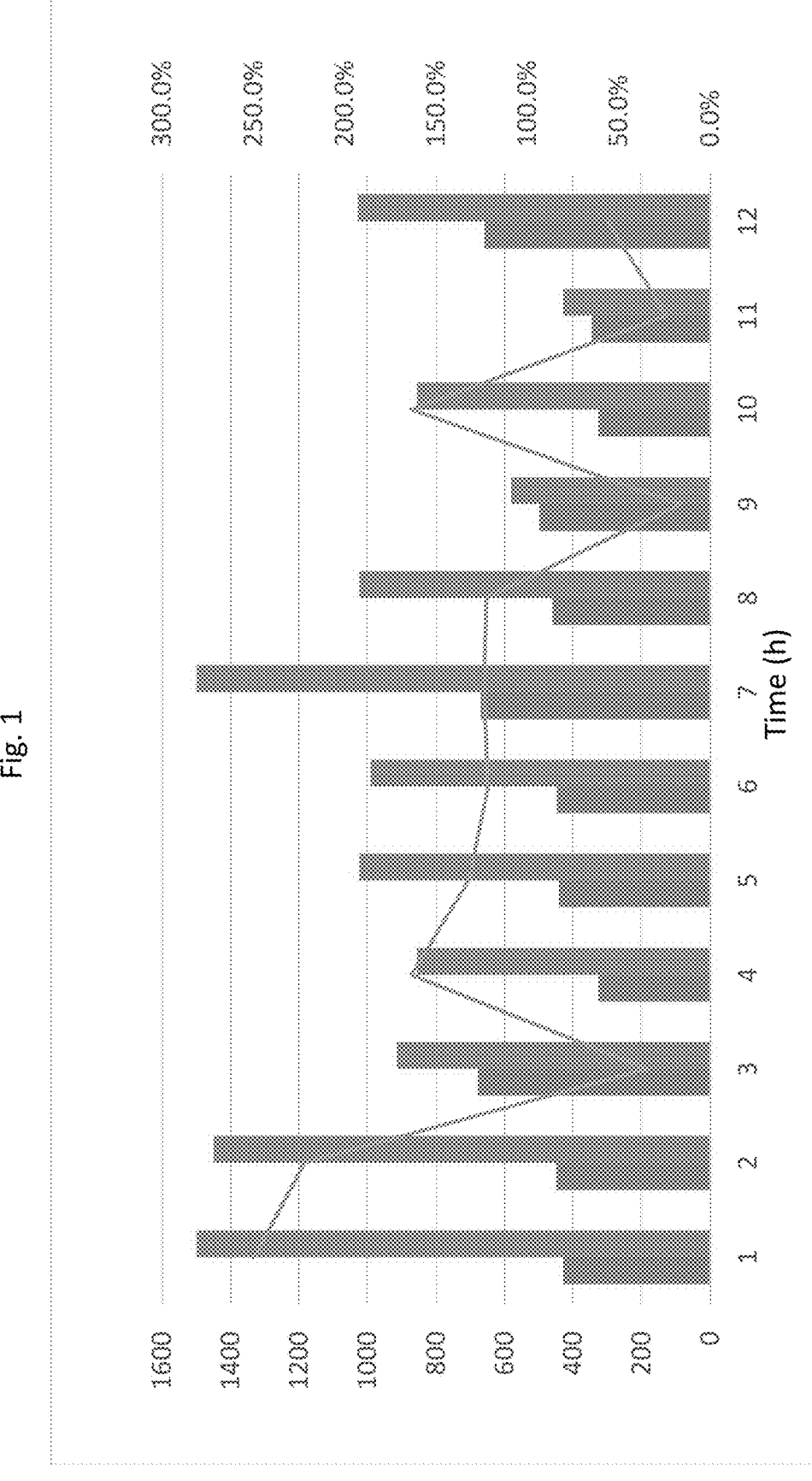
FIG. 1 is a graph of average blood serum testosterone level versus time of male subjects who have been bucally administered the present invention.

FIG. 1 shows the averaged results of the lotion of Example 1 administered buccally to volunteers by swabbing the gums with the lotion using a cotton swab. Trials using men who had been on an injection regime, after a two week wash out, achieved an average increase of 148% over their baseline total blood serum testosterone levels. The data is shown in FIG. 1.

Figure 2:
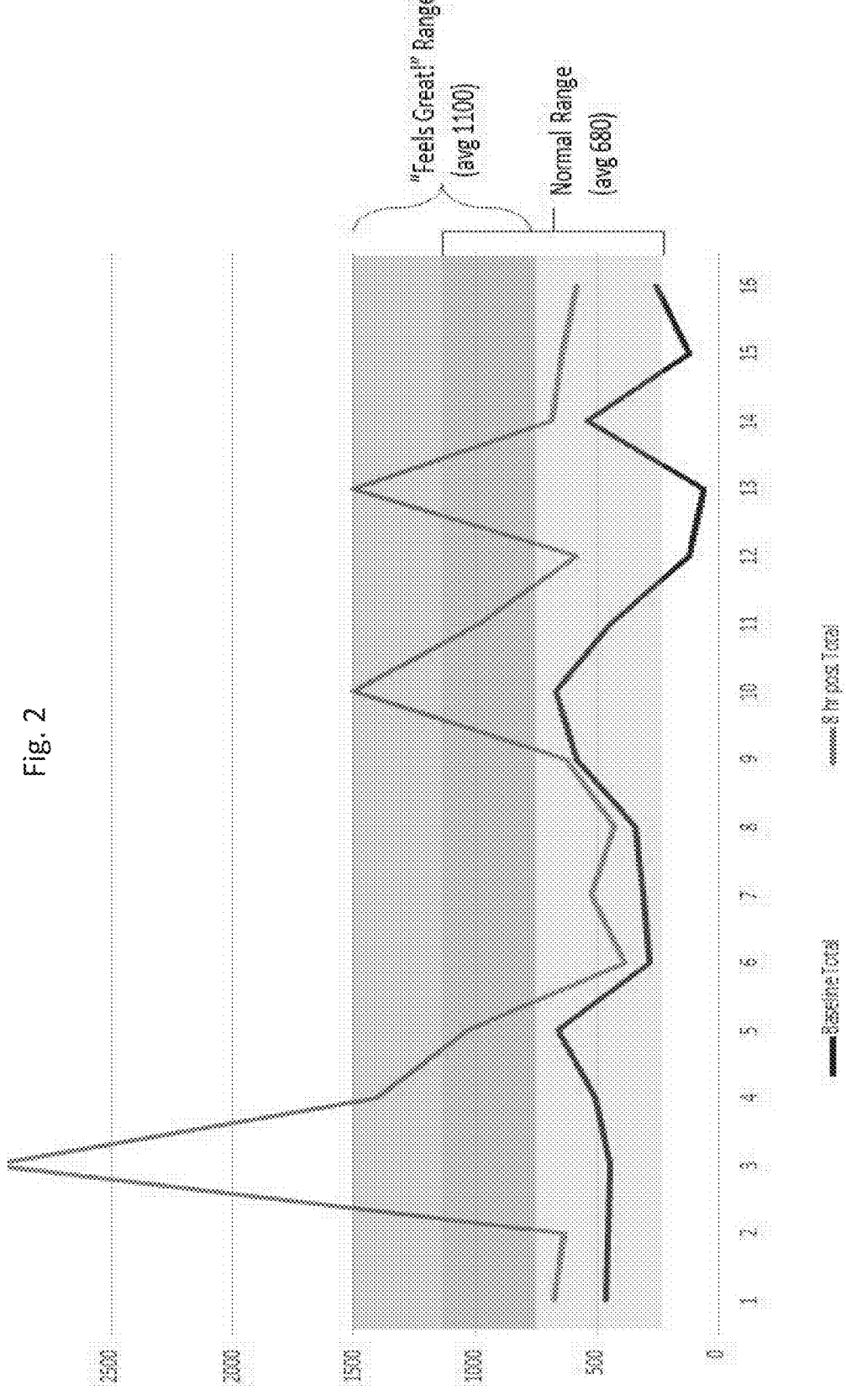
FIG. 2 is a graph of average blood serum testosterone level versus time for men who have been bucally administered the present invention.

FIG. 2 shows the averaged results of the lotion of Example 1 administered buccally to men ranging in age from 35-65 by swabbing the guns with the lotion using a cotton swab. Therapeutic levels are achieved for 12-24 hours with daily use. The average increase for men vs baseline was 148% for total testosterone and 185% for free testosterone.

FIG. 3 is a bar graph showing the blood serum testosterone levels of six men administered the lotion of Example 1 by swabbing the gums with the lotion using a cotton swab. The subjects averaged a nearly 300% increase in testosterone levels.

FIG. 4 shows the results of a pharmacokinetic study of the lotion of Example 1 applied to the exterior lip of male subjects using a cotton swab. The 72 h pharmacokinetic study demonstrated extended action a full day, although some individuals reported the method as ineffective. The hypothesis for inconsistency relates to the condition of the lip and whether it is cracked or chapped.

FIG. 5 show the results of a pharmacokinetic study of the present invention administered to the gums of male neutered dogs. A therapeutic effect was observed for up to 10 h.

Examples 2 and 3 were prepared according to the method of Example 1.

| RM # | Ingredient | Weight | % |
|---|---|---|---|
| | Example 2, 5 wt. % Testosterone | | |
| 720 | Atmos 300K | 14.0 | 7.00% |
| 223 | Testosterone Micro USP | 10.0 | 5.00% |
| 1268 | Pure Extra Virgin Sesame Expeller Pressed Oil | 6.0 | 3.00% |

-continued

| RM # | Ingredient | Weight | % |
|---|---|---|---|
| | Example 2, 5 wt. % Testosterone | | |
| 997 | Sorbitol Solution 70% USP (30% water) | 85.0 | 42.50% (12.75% water, 29.75% sorbitol) |
| 995 | Glycerin, USP 99.7% Excipient/Food use | 85.0 | 42.50% |
| | Total | 200.0 | |

| RM # | Ingredient | Weight | % |
|---|---|---|---|
| | Example 3, 10 wt. % Testosterone | | |
| 720 | Atmos 300K | 14.00 | 7.00% |
| 223 | Testosterone Micro USP | 20.00 | 10.00% |
| 1502 | Sweet Almond Oil | 10.00 | 5.00% |
| 529 | purified water (Distilled) | 20.00 | 10.00% |
| 997 | Sorbitol Solution 70% USP | 68.00 | 34.00% (10.2% water, 23.8% sorbitol) |
| 995 | Glycerin, USP 99.7% Excipient/Food use | 68.00 | 34.00% |
| Total | | 300.00 | 100.00% |

The embodiments were chosen and described to best explain the principles of the invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The invention claimed is:

1. A method of preparing a transmucosal testosterone release composition, comprising combining:

A) an aqueous phase comprising an aqueous solution or suspension containing at least one humectant;

wherein the at least one humectant is present in the aqueous phase in the range of about 50 to 99 wt. %, and B) an oil phase comprising oil soluble testosterone, at least one non-water soluble surfactant, and optionally at least one oil, wherein the at least one surfactant is present in the oil phase in the range of about 1 to 99.999 wt. %;

wherein the aqueous phase is added to the oil phase in a weight ratio of about 3:1 to 49:1;

wherein the non-water soluble surfactant is present in the composition in an amount in the range of about 1 to 15 wt. %;

wherein the humectant is present in the composition in an amount in the range of about 50 wt. % to about 90 wt. %;

wherein the oil soluble testosterone is present in the composition in an amount in the range of about 0.001 to 25.00 wt. % wherein the non-water soluble surfactant has an HLB of less than 4;

wherein the non-water soluble surfactant is selected from the group consisting of acetylated monoglycerides, glycerol dioleate, sorbitan tristearate, glycerol monooleate, propylene glycol monoglyceride, propylene glycol diglyceride and combinations thereof;

wherein the testosterone is the native form of testosterone;

wherein the aqueous phase is encapsulated by the oil phase; and wherein the composition is a lotion that is viscous, pourable, non-water dispersible, hydrophobic and has extended release properties of 12 hours or more elevated blood serum testosterone levels over baseline blood serum testosterone levels.

2. The method of claim 1, wherein the humectant is a combination of glycerine and high fructose corn syrup, wherein the high fructose corn syrup contains about 55 wt. % fructose, 21 wt. % glucose and 24 wt. % water.

3. The method of claim 1, wherein the humectant is present in the composition from about 75 wt. % to about 90 wt. %.

4. The method of claim 1, wherein the humectant is selected from the group consisting of glycerine, lactic acid, polyols, propylene glycol, high fructose corn syrup, and sorbitol, wherein the high fructose corn syrup contains about 55 wt. % fructose, 21 wt. % glucose and 24 wt. % water.

5. The method of claim 4, wherein the sorbitol is non-crystallizing liquid sorbitol.

6. The method of claim 1, wherein the humectant is a combination of glycerine and sorbitol.

7. A transmucosal testosterone delivery composition comprising:

A) an aqueous solution or suspension comprising at least one humectant, and wherein the at least one humectant is present in the aqueous phase in the range of about 50 to 99 wt. %, and B) an oil phase comprising testosterone in the range of about 0.001 to 25.0 wt. %, at least one surfactant, and optionally at least one oil, wherein the at least one surfactant is present in the oil phase in the range of about 1 to 99.999 wt. %; and wherein the ratio of the aqueous phase to the oil phase is about 3:1 to 49:1 to provide the lotion; wherein lotion is hydrophobic and has sustained release properties, and wherein the humectant is present in the composition of about 50 wt. % to about 93 wt. %.

8. A method of preparing transmucosal testosterone delivery composition, comprising mixing:

about 50 to 93 wt. % humectant;

about 1 to 50 wt. % water;

about 0.001 to 25.00 wt. % oil soluble testosterone;

about 0 to 25 wt. % oil;

about 15 to 5 wt. % non-water soluble surfactant;

wherein the non-water soluble surfactant has an HLB of less than 4;

wherein the non-water soluble surfactant is selected from the group consisting of acetylated monoglycerides, glycerol dioleate, sorbitan tristearate, glycerol monooleate, propylene glycol monoglyceride, propylene glycol diglyceride and combinations thereof;

wherein the testosterone is the native form of testosterone;

wherein the aqueous phase is encapsulated by an oil phase; and wherein the composition is a lotion that is viscous, pourable, non-water dispersible, hydrophobic and has extended release properties of 12 hours or more elevated blood serum testosterone levels over baseline blood serum testosterone levels.

9. The method of claim 8, wherein the humectant is present in the composition from about 75 wt % to about 93 wt %.

10. The method of claim 9, wherein the humectant is selected from the group consisting of glycerine, lactic acid, polyols, propylene glycol, high fructose corn syrup, and sorbitol, wherein the high fructose corn syrup contains about 55 wt. % fructose, 21 wt. % glucose and 24 wt. % water.

11. The of claim 10, wherein the sorbitol is non-crystallizing liquid sorbitol.

12. The method of claim 10, wherein the humectant is a combination of glycerine and sorbitol.

13. The method of claim 10, wherein the humectant is a combination of the glycerine and the high fructose corn syrup.

14. The method of claim 10, wherein the ratio of glycerine to sorbitol is in the range of about 2:1 to 1:2.

15. The method of claim 13, wherein the ratio of the glycerine to the high fructose corn syrup is in the range of about 10:1 to about 4:1.

\* \* \* \* \*